US009693442B2

(12) United States Patent
Ikeda

(10) Patent No.: US 9,693,442 B2
(45) Date of Patent: Jun. 27, 2017

(54) PLASMA GENERATION PROVISION, INTERNAL COMBUSTION ENGINE AND ANALYSIS PROVISION

(75) Inventor: Yuji Ikeda, Kobe (JP)

(73) Assignee: IMAGINEERING, INC., Hyogo (JP)

( * ) Notice: Subject to any disclaimer, the term of this patent is extended or adjusted under 35 U.S.C. 154(b) by 344 days.

(21) Appl. No.: 14/233,103

(22) PCT Filed: Jun. 27, 2012

(86) PCT No.: PCT/JP2012/066350
§ 371 (c)(1), (2), (4) Date: Apr. 24, 2014

(87) PCT Pub. No.: WO2013/011810
PCT Pub. Date: Jan. 24, 2013

(65) Prior Publication Data

US 2014/0261271 A1 Sep. 18, 2014

(30) Foreign Application Priority Data

Jul. 16, 2011 (JP) ................................ 2011-157285
Sep. 22, 2011 (JP) ................................ 2011-207320

(51) Int. Cl.
*F02B 3/00* (2006.01)
*H05H 1/46* (2006.01)
(Continued)

(52) U.S. Cl.
CPC ................ *H05H 1/46* (2013.01); *F02P 3/04* (2013.01); *F02P 9/007* (2013.01); *F02P 23/045* (2013.01);
(Continued)

(58) Field of Classification Search
CPC .. F02P 3/04; F02P 9/007; F02P 23/045; F02P 23/04; G01N 21/67; G01N 21/68;
(Continued)

(56) References Cited

U.S. PATENT DOCUMENTS 3,934,566 A 1/1976 Ward
2002/0017271 A1* 2/2002 Suckewer ............ F02D 19/081 123/297
(Continued)

FOREIGN PATENT DOCUMENTS

JP 51-77719 A 7/1976
JP 2009-281188 A 12/2009
(Continued)

OTHER PUBLICATIONS

International Search Report dated Nov. 6, 2012, issued in corresponding application No. PCT/JP2012/066350.

*Primary Examiner* — Hai Huynh
*Assistant Examiner* — Gonzalo Laguarda
(74) *Attorney, Agent, or Firm* — Westerman, Hattori, Daniels & Adrian, LLP

(57) ABSTRACT

To make it easy to adjust a location of an emission antenna in a plasma generation device that generates plasma by a discharge and enlarges the plasma by an electromagnetic wave. A plasma generation device 30 includes an electromagnetic wave generation device 31, an emission antenna 16, a high voltage generation device 14, and a discharge electrode 15. The emission antenna 16 forms a discharge gap together with the discharge electrode 15 which a high voltage outputted from the high voltage generation device 14 is applied to. The plasma generation device 30 enlarges discharge plasma using the electromagnetic wave emitted from the emission antenna 16 caused by the electromagnetic wave outputted from the electromagnetic wave generation device 31, where the discharge plasma is generated at the discharge gap by an output of a high voltage from the high voltage generation device 14.

11 Claims, 10 Drawing Sheets

(51) Int. Cl.

| | |
|---|---|
| ***G01N 21/67*** | (2006.01) |
| ***G01N 21/68*** | (2006.01) |
| ***F02P 23/04*** | (2006.01) |
| ***H01T 13/50*** | (2006.01) |
| ***F02P 3/04*** | (2006.01) |
| ***F02P 9/00*** | (2006.01) |

(52) U.S. Cl.
CPC ............. *G01N 21/67* (2013.01); *G01N 21/68* (2013.01); *H01T 13/50* (2013.01); *H05H 2001/463* (2013.01)

(58) Field of Classification Search
CPC ........... H01T 13/50; H01T 13/32; H05H 1/46; H05H 2004/463
USPC .................... 123/169 EL, 469 G, 154, 143 B
See application file for complete search history.

(56) References Cited

U.S. PATENT DOCUMENTS

| | | | | |
|---|---|---|---|---|
| 2010/0187968 A1* | 7/2010 | Ikeda .................... | F02P 23/045 313/134 | |
| 2012/0097140 A1* | 4/2012 | Kusunoki ............... | F02P 9/002 123/620 | |
| 2012/0258016 A1 | 10/2012 | Makita et al. | | |
| 2013/0148254 A1* | 6/2013 | Katsuraya ................. | F02P 3/01 361/253 | |

FOREIGN PATENT DOCUMENTS

| | | | |
|---|---|---|---|
| JP | 2010-25869 | A | 2/2010 |
| JP | 2010-96109 | A | 4/2010 |
| WO | 2009/008518 | A1 | 1/2009 |
| WO | 2009/008520 | A1 | 1/2009 |

* cited by examiner

PLASMA GENERATION PROVISION, INTERNAL COMBUSTION ENGINE AND ANALYSIS PROVISION

TECHNICAL FIELD

The present invention relates to a plasma generation device that utilizes energy of an electromagnetic wave, an internal combustion engine that includes the plasma generation device, and an analysis device that includes the plasma generation device.

BACKGROUND ART

Conventionally, there is known a plasma generation device that utilizes energy of an electromagnetic wave. For example, Japanese Unexamined Patent Application, Publication No. 2007-113570 discloses an ignition device that constitutes a plasma generation device of this kind.

The ignition device disclosed by Japanese Unexamined Patent Application, Publication No. 2007-113570 is provided in an internal combustion engine. The ignition device emits a microwave to a combustion chamber before or after ignition of fuel air mixture, thereby causing a plasma discharge. The ignition device generates local plasma using a discharge of an ignition plug so that the plasma is generated in a high pressure field, and grows the plasma by a microwave. The local plasma is generated at a discharge gap between a tip end part of an anode terminal and a ground terminal part.

THE DISCLOSURE OF THE INVENTION

Problems to be Solved by the Invention

In a conventional internal combustion engine, plasma generated by a discharge (hereinafter, referred to as "discharge plasma") may not be enlarged using an electromagnetic wave when a location relationship between a discharge gap and an emission antenna changes slightly. It is difficult to adjust the location of the emission antenna in relation to the discharge gap such that the electromagnetic wave can enlarge the discharge plasma.

The present invention has been made in view of the above described circumstances, and it is an object of the present invention to ease a location adjustment of an emission antenna in a plasma generation device that allows an electromagnetic wave to enlarge plasma generated by a discharge.

Means for Solving the Problems

In accordance with a first aspect of the present invention, there is provided a plasma generation device including: an electromagnetic wave generation device that generates an electromagnetic wave; an emission antenna for emitting the electromagnetic wave outputted from the electromagnetic wave generation device to a target space; a high voltage generation device that generates a high voltage; and a discharge electrode that is provided in the target space and is applied with the high voltage outputted from the high voltage generation device. The emission antenna forms a discharge gap together with the discharge electrode. The plasma generation device enlarges discharge plasma using the electromagnetic wave emitted from emission antenna caused by the electromagnetic wave outputted from the electromagnetic wave generation device, where the discharge plasma is generated at the discharge gap by an output of a high voltage from the high voltage generation device.

According to the first aspect of the present invention, the emission antenna serves a role of a ground electrode of an ignition plug, for example. The discharge plasma is generated between the emission antenna that emits the electromagnetic wave and the discharge electrode that is applied with the high voltage. In the vicinity of the emission antenna, an insulation breakdown occurs, and free electrons are emitted from molecules around. In the vicinity of the emission antenna, an electric field of the electromagnetic wave is concentrated and accelerates the free electrons. The accelerated free electrons collide with and ionize ambient molecules. Also, free electrons generated by the ionization are accelerated by the electric field and ionize ambient molecules. Thus, avalanche-like ionization occurs. As a result of this, the discharge plasma is enlarged. According to the first aspect of the present invention, it is configured such that free electrons that serve as triggers of electromagnetic wave plasma are emitted in the vicinity of the emission antenna.

In accordance with a second aspect of the present invention, in addition to the first aspect of the present invention, the emission antenna is electrically grounded.

In accordance with a third aspect of the present invention, in addition to the first or the second aspect of the present invention, the emission antenna is formed in a shape of a letter C or a ring in a manner to surround the discharge electrode.

In accordance with a fourth aspect of the present invention, in addition to the first aspect of the present invention, the plasma generation device includes in the target space a secondary electrode provided in a state of being electrically grounded or floating at a location where a discharge does not occur between the discharge electrode and the secondary electrode even if a high voltage is applied to the discharge electrode from the high voltage generation device. Assuming that the discharge gap between the emission antenna and the discharge electrode as a first discharge gap, a second discharge gap is formed between the emission antenna and the secondary electrode.

In accordance with a fifth aspect of the present invention, there is provided a plasma generation device including: an electromagnetic wave generation device that generates an electromagnetic wave; an emission antenna for emitting to a target space the electromagnetic wave outputted from the electromagnetic wave generation device; a high voltage generation device that generates a high voltage; a discharge electrode that is provided in the target space and is applied with the high voltage outputted from the high voltage generation device; a first electrode that forms a first discharge gap together with the discharge electrode; and a second electrode that forms a second discharge gap together with the first electrode. The plasma generation device enlarges discharge plasma at the first discharge gap and the second discharge gap respectively using the electromagnetic wave emitted from the emission antenna caused by the electromagnetic wave outputted from the electromagnetic wave generation device, where the discharge plasma is generated at the first discharge gap and the second discharge gap by an output of a high voltage from the high voltage generation device.

In accordance with a sixth aspect of the present invention, there is provided an internal combustion engine including: a plasma generation device according to any one of the first to fifth aspects of the present invention; and an internal combustion engine main body formed with a combustion chamber. The emission antenna and the discharge electrode are provided in the internal combustion engine main body so that the discharge gap locates in the combustion chamber.

In accordance with a seventh aspect of the present invention, there is provided an analysis device including: a plasma generation device according to the first or the second aspect of the present invention, which is adapted to turn a target analyte into a plasma state; and an optical analysis device that analyzes the target analyte by analyzing analysis light emitted from a region where the plasma of the target analyte is generated by the plasma generation device.

In accordance with an eighth aspect of the present invention, in addition to the seventh aspect of the present invention, the analysis device includes a casing, which is provided with the emission antenna and the discharge electrode, and partitions the target space. The emission antenna is formed in a rod-like shape and protrudes toward the discharge electrode from a surface facing toward a surface having the discharge electrode provided thereon from among surfaces of the casing.

In accordance with a ninth aspect of the present invention, in addition to the seventh aspect of the present invention, the plasma generation device sustains the plasma enlarged by the electromagnetic wave by continuously emitting the electromagnetic wave from the emission antenna, and the optical analysis device analyzes the target analyte using a time integral value of emission intensity of the analysis light over a plasma sustain period during which the plasma generation device sustains the plasma.

In accordance with a tenth aspect of the present invention, in addition to the ninth aspect of the present invention, the plasma generation device causes the emission antenna to emit the electromagnetic wave as a continuous wave during the plasma sustain period.

In accordance with an eleventh aspect of the present invention, in addition to the tenth aspect of the present invention, during the plasma sustain period, the target analyte is transferred to a region where the plasma sustained by the plasma generation device is present, and turned into the plasma state.

Effect of the Invention

According to the present invention, it is configured such that an insulation breakdown is caused to occur between the discharge electrode and the emission antenna so that free electrons that serve as triggers of the electromagnetic wave plasma are emitted in the vicinity of the emission antenna. Accordingly, since the discharge plasma is enlarged by the electromagnetic wave as long as the emission antenna is positioned in relation to the discharge gap so that the insulation breakdown occurs by the high voltage, it is possible to easily adjust the location of the emission antenna.

BEST MODE FOR CARRYING OUT THE INVENTION

Figure 1:
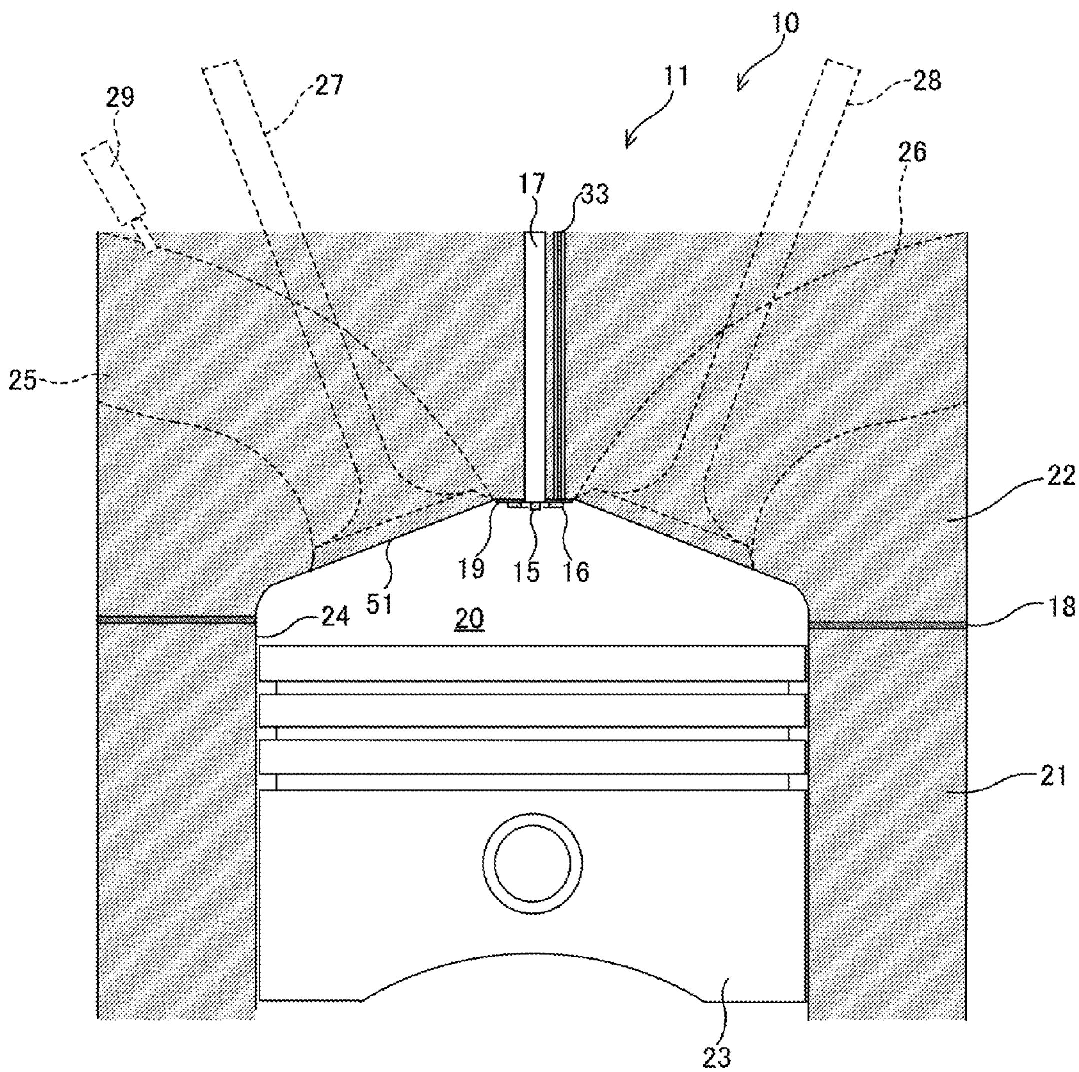
FIG. 1 is a vertical cross sectional view of an internal combustion engine according to a first embodiment.

In the following, a detailed description will be given of embodiments of the present invention with reference to drawings. It should be noted that the following embodiments are merely preferable examples, and do not limit the scope of the present invention, applied field thereof, or application thereof.

<First Embodiment>

The first embodiment is directed to an internal combustion engine 10 that includes a plasma generation device 30 according to the present invention. The internal combustion engine 10 is a reciprocating type internal combustion engine in which pistons 23 reciprocate. The internal combustion engine 10 includes an internal combustion engine main body 11 and a plasma generation device 30. In the internal combustion engine 10, a combustion cycle is repeated in which fuel air mixture in a combustion chamber 20 is ignited and combusted by way of plasma generated by the plasma generation device 30.

<Internal Combustion Engine Main Body>

As shown in FIG. 1, the internal combustion engine main body 11 includes a cylinder block 21, a cylinder head 22, and the pistons 23. The cylinder block 21 is formed with a plurality of cylinders 24 each having a circular cross section. Inside of each cylinder 24, the piston 23 is reciprocatably mounted. The piston 23 is connected to a crankshaft (not shown) via a connecting rod (not shown). The crankshaft is rotatably supported by the cylinder block 21. While the piston 23 reciprocates in each cylinder 24 in an axial direction of the cylinder 24, the connecting rod converts the reciprocal movement of the piston 23 to rotational movement of the crankshaft.

The cylinder head 22 is placed on the cylinder block 21, and a gasket 18 intervenes between the cylinder block 21 and the cylinder head 22. The combustion chamber 20 has a circular cross section and formed by the cylinder head 22 along with the cylinder 24 and the piston 23. A diameter of the combustion chamber 20 is equal to, for example, approximately a half wavelength of the microwave emitted from an emission antenna 16, which will be described later.

Figure 2:
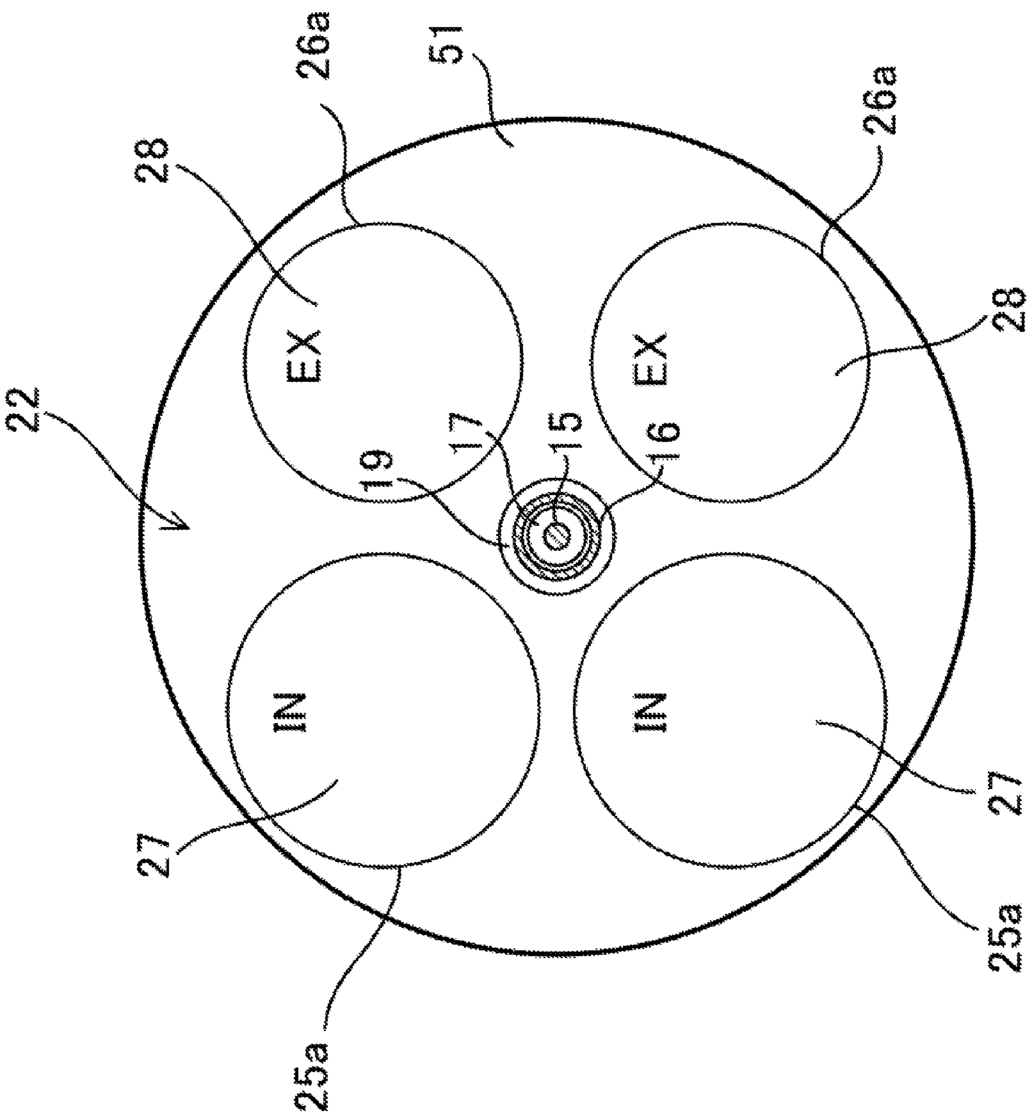
FIG. 2 is a front view of a ceiling surface of a combustion chamber of the internal combustion engine according to the first embodiment.

The cylinder head 22 is provided with one discharge electrode 15 that constitutes a part of a discharge device 12 for each cylinder 24. Each discharge electrode 15 is provided at a tip end of a cylindrical shaped insulator 17 embedded in the cylinder head 22. As shown in FIG. 2, each discharge electrode 15 locates at a central part of a ceiling surface 51 of the combustion chamber 20. The ceiling surface 51 is a surface of the cylinder head 22 and exposed toward the combustion chamber 20.

The cylinder head 22 is formed with intake ports 25 and exhaust ports 26 for each cylinder 24. Each intake port 25 is provided with an intake valve 27 for opening and closing an intake side opening 25*a* of the intake port 25, and an injector 29 for injecting fuel. On the other hand, each exhaust port 26 is provided with an exhaust valve 28 for opening and closing an exhaust side opening 26*a* of the exhaust port 26. The internal combustion engine 10 is designed such that the intake ports 25 form a strong tumble flow in the combustion chamber 20.

<Plasma Generation Device>

Figure 3:
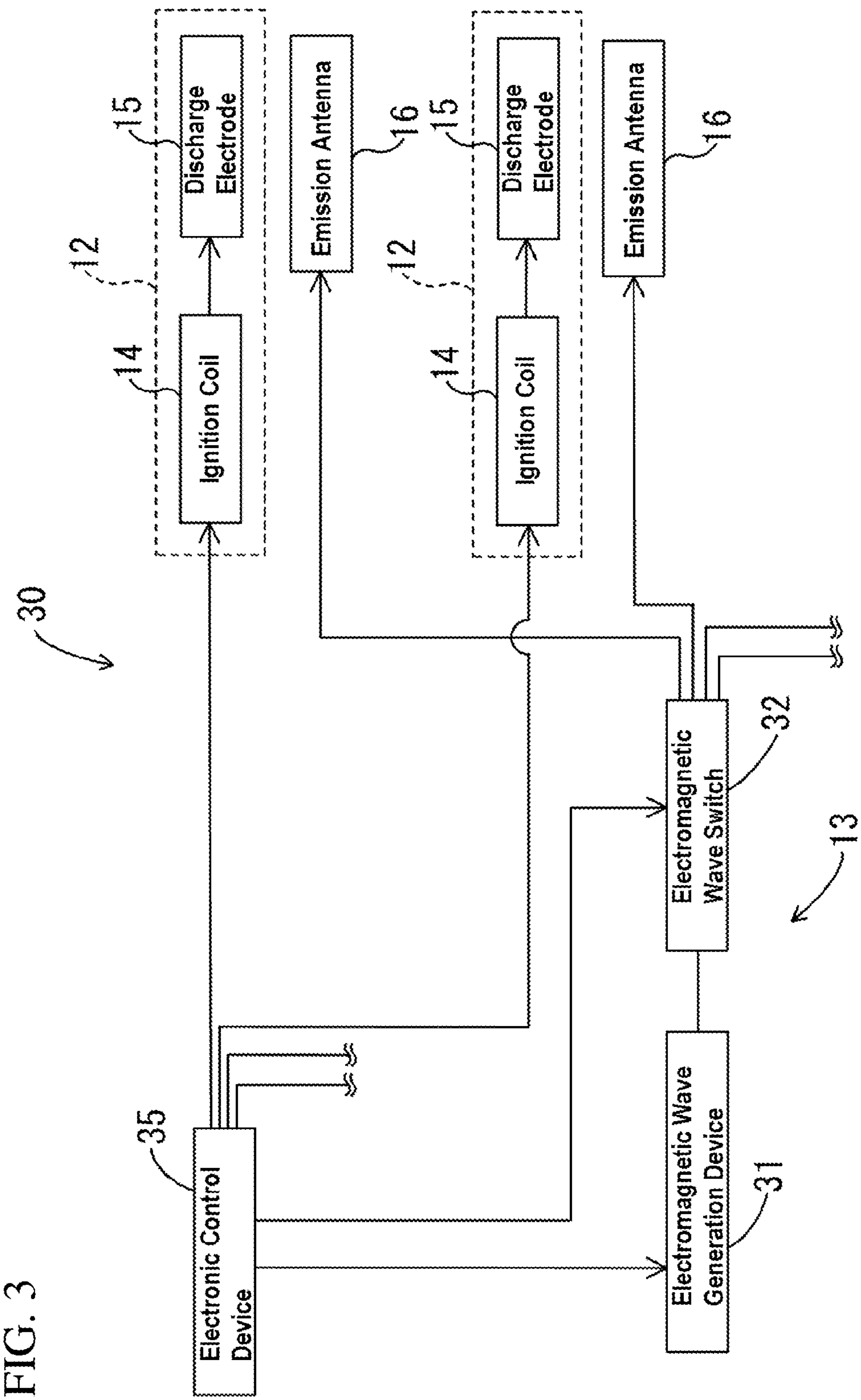
FIG. 3 is a block diagram of a plasma generation device according to the first embodiment.

As shown in FIG. 3, the plasma generation device 30 includes the discharge device 12 and an electromagnetic wave emission device 13.

The discharge device 12 is provided for each combustion chamber 20. Each discharge device 12 includes an ignition coil 14 (a high voltage generation device) that generates a high voltage pulse and the discharge electrode 15 which the high voltage pulse outputted from the ignition coil 14 is applied to.

The ignition coil 14 is connected to a direct current power supply (not shown). The ignition coil 14, upon receiving an ignition signal from an electronic control device 35, boosts a voltage applied from the direct current power supply, and outputs the boosted high voltage pulse to the discharge electrode 15.

A discharge electrode 15 is provided in the cylinder head 22 at an end surface of an insulator 17 that passes through the cylinder head 22. An electric wire (not shown) for electrically connecting the ignition coil 14 and the discharge electrode 15 is embedded inside of the insulator 17. The electric wire and the discharge electrode 15 are both insulated from the cylinder head 22 by the insulator 17. The discharge electrode 15 forms a discharge gap together with an emission antenna 16, which will be described later. When the high voltage pulse is supplied to the discharge electrode 15, a spark discharge occurs at the discharge gap.

The electromagnetic wave emission device 13 includes an electromagnetic wave generation device 31, an electromagnetic wave switch 32, and the emission antenna 16. One electromagnetic wave generation device 31 and one electromagnetic wave switch 32 are provided for the electromagnetic wave emission device 13, and the emission antenna 16 is provided for each combustion chamber 20.

The electromagnetic wave generation device 31, upon receiving an electromagnetic wave drive signal from the electronic control device 35, repeatedly outputs a microwave pulse at a predetermined duty cycle. The electromagnetic wave drive signal is a pulse signal. The electromagnetic wave generation device 31 repeatedly outputs the microwave pulse during a period of time of the pulse width of the electromagnetic wave drive signal. In the electromagnetic wave generation device 31, a semiconductor oscillator generates the microwave pulse. In place of the semiconductor oscillator, any other oscillator such as a magnetron may be employed.

The electromagnetic wave switch 32 includes an input terminal and a plurality of output terminals provided for respective emission antennae 16. The input terminal is connected to the electromagnetic wave generation device 31. Each output terminal is connected to the corresponding emission antenna 16. The electromagnetic wave switch 32 switches in turn a supply destination of the microwave outputted from the electromagnetic wave generation device 31 from among the plurality of emission antennae 16 under a control of the electronic control device 35.

The emission antenna 16 is formed in a circular shape and provided on the ceiling surface 51 of the combustion chamber 20 in a manner to surround the discharge electrode 15. The discharge electrode 15 and the emission antenna 16 are arranged concentrically with each other. The emission antenna 16 is provided on an insulation layer 19 formed in a ring shape on the ceiling surface 51 of the combustion chamber 20. The emission antenna 16 is electrically connected to the output terminal of the electromagnetic wave switch 32 through a coaxial line 33 embedded in the cylinder head 22. The emission antenna 16 may be formed in a C-letter shape.

According to the first embodiment, a distance between the discharge electrode 15 and the emission antenna 16 is configured so that the high voltage pulse outputted from the ignition coil 14 causes an insulation breakdown to occur. The distance between the discharge electrode 15 and the emission antenna 16 may be, for example, from 2 to 3 mm. The emission antenna 16 serves a role as a ground electrode of an ignition plug. Although the emission antenna 16 is grounded in the first embodiment, the emission antenna 16 may not necessarily be grounded. The plasma generation device 30, while causing the ignition coil 14 to output the high voltage pulse so as to generate the discharge plasma at the discharge gap, causes the electromagnetic wave generation device 31 to output the microwave so that the emission antenna 16 emits the microwave, thereby enlarging the discharge plasma and generating comparatively large microwave plasma.

<Plasma Generation Operation>

A plasma generation operation of the plasma generation device 30 will be described hereinafter.

At an ignition timing when the piston 23 locates immediately before the compression top dead center, the internal combustion engine 10 performs an ignition operation of igniting the fuel air mixture by way of the plasma generated by the plasma generation device 30. During the ignition operation, the electronic control device 35 outputs the ignition signal and the electromagnetic wave drive signal at the same timing. Then, the ignition coil 14, upon receiving the ignition signal, outputs the high voltage pulse, and the high voltage pulse is applied to the discharge electrode 15. As a result of this, the spark discharge occurs at the discharge gap between the discharge electrode 15 and the emission antenna 16.

Meanwhile, in the electromagnetic wave emission device 13, the electromagnetic wave generation device 31, upon receiving the electromagnetic wave drive signal, repeatedly outputs the microwave pulse during the period of time of the pulse width of the electromagnetic wave drive signal. The microwave pulse is repeatedly emitted from the emission antenna 16. As a result of this, the discharge plasma generated by the spark discharge absorbs energy of the microwave and is enlarged, and the fuel air mixture is ignited by the enlarged microwave plasma. A flame spreads outwardly from an ignition location where the fuel air mixture is ignited toward a wall surface of the cylinder 24.

According to the first embodiment, the electronic control device 35 outputs the electromagnetic wave drive signal immediately after the ignition of the fuel air mixture, as well. Then, the electromagnetic wave generation device 31 repeatedly outputs the microwave pulse during the period of time of the pulse width of the electromagnetic wave drive signal. The microwave pulse is repeatedly emitted from the emission antenna 16.

The microwave pulse is emitted before a flame surface passes through the location of the emission antenna 16. In the vicinity of the emission antenna 16, the microwave forms a strong electric field region having an electric field relatively strong in intensity in the combustion chamber 20. The flame surface receives energy from the microwave while passing through the strong electric field region and accelerates the propagation speed. When the microwave energy is strong, the microwave plasma is generated in the strong electric field region before the flame surface passes therethrough. Since active species such as OH radicals are generated in a generation region where the microwave plasma is generated, the flame surface further accelerates the propagation speed while passing through the strong electric field region owing to the active species.

<Effect of First Embodiment>

According to the first embodiment, it is configured such that the insulation breakdown is caused to occur between the discharge electrode 15 and the emission antenna 16 so that free electrons that serve as triggers of the microwave plasma are emitted in the vicinity of the emission antenna 16. Accordingly, as long as the emission antenna 16 is positioned in relation to the discharge electrode 15 at a location where the insulation breakdown can occur by the high voltage, since the discharge plasma is enlarged by the microwave, it is possible to easily adjust the location of the emission antenna 16.

Furthermore, according to the first embodiment, the emission antenna 16 is provided in a manner to surround the discharge electrode 15, the insulation breakdown occurs around the discharge electrode 15. The microwave energy is absorbed by the discharge plasma around the discharge electrode 15. Therefore, it is possible to generate large microwave plasma. Since the large microwave plasma can be generated, the temperature of a plasma region decreases as a whole in comparison with a case in which the discharge plasma between a central electrode and a ground electrode of an ordinary ignition plug is enlarged by the microwave. Accordingly, active species such as OH radicals hardly disappear, and it is possible to effectively accelerate the propagation speed of the flame.

<Second Embodiment>

Figure 4:
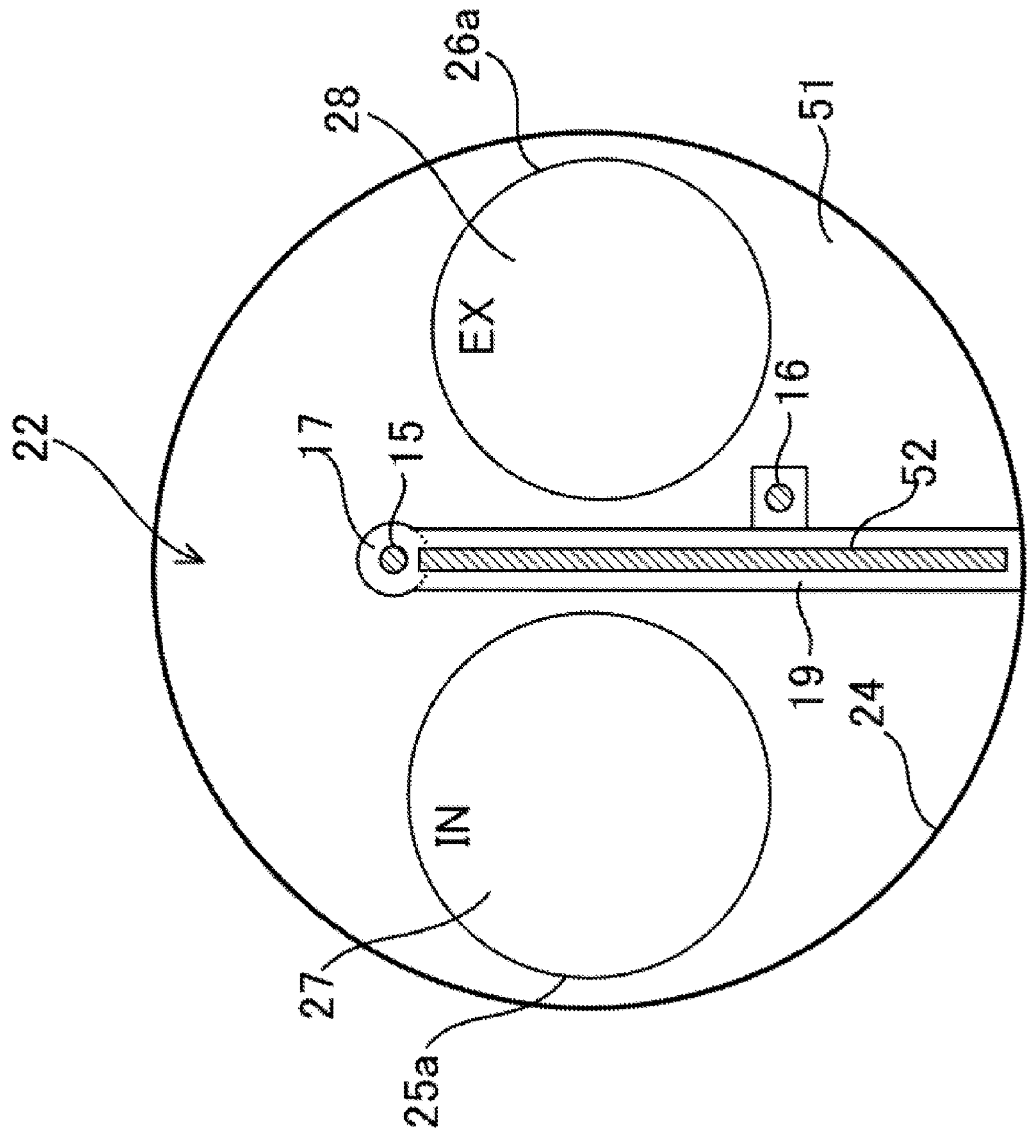
FIG. 4 is a front view of a ceiling surface of a combustion chamber of an internal combustion engine according to a second embodiment.

The second embodiment is directed to a two-valve internal combustion engine 10 provided with one intake valve 27 and one exhaust valve 28, as shown in FIG. 4. A discharge electrode 15 is provided on the ceiling surface 51 of the combustion chamber 20 at a location off-center with respect to the center of the ceiling surface 51. Furthermore, a receiving antenna 52 in the form of a rod-like shape is provided on the ceiling surface 51 of the combustion chamber 20. The receiving antenna 52 constitutes a secondary electrode provided at a location where a discharge does not occur between the secondary electrode and the discharge electrode 15 even if the high voltage is applied from the ignition coil 14 to the discharge electrode 15.

The receiving antenna 52 is provided on a region between an intake side opening 25*a* and an exhaust side opening 26*a*. The receiving antenna 52 extends in a direction perpendicular to a line connecting a center of the intake side opening 25*a* and a center of the exhaust side opening 26*a*. The receiving antenna 52 extends from the vicinity of the discharge electrode 15 to the vicinity of the wall surface of the cylinder 24. The receiving antenna 52 is provided on an insulation layer 19 formed in an approximately square shape on the ceiling surface 51 of the combustion chamber 20. The receiving antenna 52 is electrically insulated from the cylinder head 22 by the insulation layer 19, and is provided in an electrically floating state. The receiving antenna 52 may be electrically grounded.

According to the second embodiment, similarly to the first embodiment, the fuel air mixture is ignited by simultaneously operating the discharge device 12 and the electromagnetic wave emission device 13. In the internal combustion engine 10, the electronic control device 35 outputs the ignition signal and the electromagnetic wave drive signal at the ignition timing when the piston 23 locates immediately before the compression dead center. Then, the high voltage pulse is applied to the discharge electrode 15, and a spark discharge occurs at a first discharge gap between the discharge electrode 15 and the receiving antenna 52. Furthermore, the discharge electrode 15 and the receiving antenna 52 are electrically conducted to each other by the discharge plasma, thereby an electric current flows through the receiving antenna 52, and thus, another spark discharge occurs at a second discharge gap between the receiving antenna 52 and the wall surface of the cylinder 24. This means that the spark discharges occur approximately simultaneously in the vicinities of both ends of the receiving antenna 52. The cylinder block 21 is electrically grounded.

Meanwhile, the electromagnetic wave generation device 31 repeatedly outputs the microwave pulse during the period of time of the pulse width of the electromagnetic wave drive signal, and the microwave pulse is repeatedly emitted from the emission antenna 16. In the vicinity of each end of the receiving antenna 52, the discharge plasma generated by each spark discharge absorbs the microwave energy and is enlarged, and the fuel air mixture is ignited by the enlarged microwave plasma. In the combustion chamber 20, flames spread from respective ignition locations in the vicinities of both ends of the receiving antenna 52, and the fuel air mixture is combusted.

The secondary electrode 52 in the rod-like shape may be employed as the emission antenna.

<Modified Example of Second Embodiment>

Figure 5:
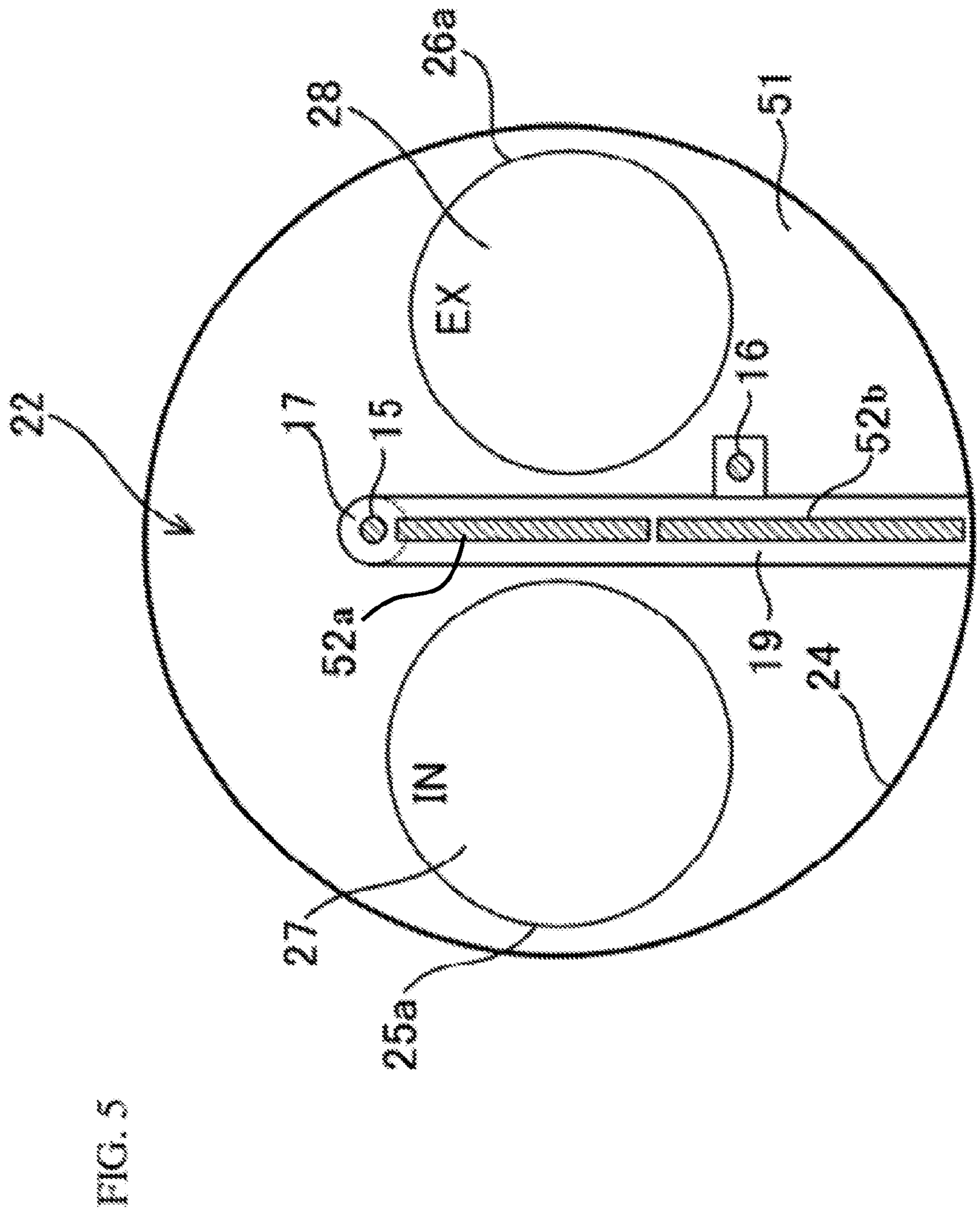
FIG. 5 is a front view of a ceiling surface of a combustion chamber of an internal combustion engine according to a modified example of the second embodiment.

In the modified example of the second embodiment, as shown in FIG. 5, there may be provided a plurality of the receiving antennae 52. According to the modified example of the second embodiment, there are provided two receiving antennae 52.

The two receiving antennae 52*a* and 52*b* are provided on a region between the intake side opening 25*a* and the exhaust side opening 26*a*. The two receiving antennae 52*a* and 52*b* are electrically insulated from the cylinder head 22 by the insulation layer 19. The first receiving antenna 52*a* constitutes a first electrode that forms a first discharge gap together with the discharge electrode 15. The second receiving antenna 52*b* constitutes a second electrode that forms a second discharge gap together with the first receiving antenna 52*a*. The second receiving antenna 52*b* forms a third discharge gap together with the wall surface of the cylinder 24.

According to the modified example of the second embodiment, when the high voltage pulse is applied to the discharge electrode 15, a spark discharge occurs at the first discharge gap. Furthermore, the discharge electrode 15 and the first receiving antenna 52*a* are electrically conducted to each other by the discharge plasma, thereby an electric current flows through the first receiving antenna 52*a*, and thus, another spark discharge occurs at the second discharge gap. Furthermore, the first receiving antenna 52*a* and the second receiving antenna 52*b* are electrically conducted to each other by the discharge plasma, thereby an electric current flows through the second receiving antenna 52*b*, and thus, another spark discharge occurs at the third discharge gap. The spark discharges occur at three locations.

Meanwhile, the emission antenna 16 repeatedly emits the microwave pulse. At each discharge gap, the discharge plasma generated by the spark discharge absorbs the microwave energy and is enlarged, and the fuel air mixture is ignited by the enlarged microwave plasma.

<Third Embodiment>

Figure 6:
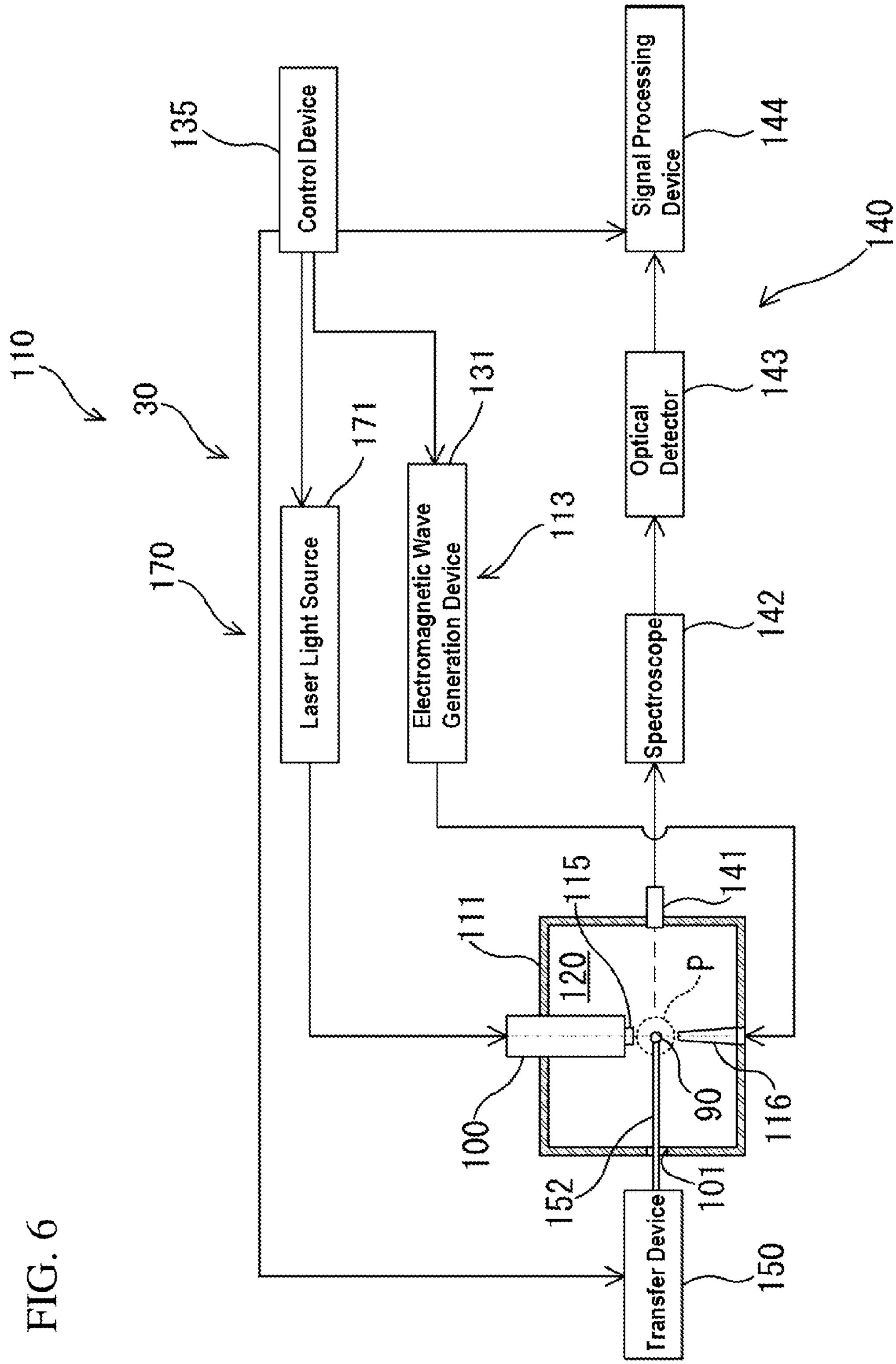
FIG. 6 is a schematic configuration diagram of an analysis device according to a third embodiment.

The third embodiment is directed to an analysis device 110 that includes the plasma generation device 30 according to the present invention. The analysis device 110 is a device that performs component analysis of a target analyte 90. The target analyte 90 may be for example, a metal or the like. The analysis device 110 is used for detecting an impure substance, for example. As shown in FIG. 6, the analysis device 110 includes a casing 111, the plasma generation device 30, an optical analysis device 140, a transfer device 150, and a control device 135. The control device 135 controls the plasma generation device 30, the optical analysis device 140, and the transfer device 150.

The casing 111 is a container in the form of an approximately cylinder-like shape. The casing 111 is attached with a plug for discharge 100 on a top surface of the casing 111, with an emission antenna 116 on a lower surface of the casing 111, and with an optical probe 141 on a side surface of the casing 111, respectively. The casing 111 is a mesh-like member. The mesh of the casing is configured such that a microwave emitted from the emission antenna 116 should not leak to outside. The casing 111 is formed on another side surface of the casing 111 with an introduction window 101 for introducing the target analyte 90 to an internal space 120 of the casing 111.

The plasma generation device 30 is a device that generates plasma in the internal space 120 of the casing 111, thereby turning the target analyte 90 into a plasma state. The plasma generation device 30 includes a discharge device 112 and an electromagnetic wave emission device 113, similarly to the first embodiment.

The discharge device 112 includes a high voltage generation device 114 and the plug for discharge 100. The high voltage generation device 114 is a device that generates a high voltage pulse. The high voltage generation device 114, upon receiving a discharge signal from the control device 135, outputs the high voltage pulse to the plug for discharge 100. While on the other hand, the plug for discharge 100 is an ignition plug for vehicle from which a ground electrode is detached. The plug for discharge 100 is provided at a tip end part thereof with a discharge electrode 115 connected to an input terminal via a conductor that passes through inside of the plug for discharge 100. The discharge electrode 115 forms a discharge gap together with an emission antenna 116, which will be described later. When the high voltage generation device 114 supplies the high voltage pulse to the discharge electrode 115 of the plug for discharge 100, an insulation breakdown occurs at the discharge gap, and a spark discharge occurs.

The electromagnetic wave emission device 113 includes an electromagnetic wave generation device 131 and the emission antenna 116. The electromagnetic wave generation device 131, upon receiving an electromagnetic wave drive signal from the control device 135, continuously outputs the microwave during a period of time of a pulse width of the electromagnetic wave drive signal. The electromagnetic wave drive signal is a pulse signal of a constant voltage value. The electromagnetic wave generation device 131 outputs the microwave as a CW (Continuous Wave) to the emission antenna 116 via a microwave transmission line. While, on the other hand, the emission antenna 116 is a rod-like shaped antenna. The emission antenna 116, when supplied with the microwave from the electromagnetic wave generation device 131, emits the microwave.

According to the third embodiment, the emission antenna 116 protrudes toward the discharge electrode 115 from the lower surface facing toward the top surface provided with the discharge electrode 115 from among the surfaces of the casing 111. A tip end of the emission antenna 116 is facing toward and spaced apart at a slight distance from the discharge electrode 115. The distance between the emission antenna 116 and the discharge electrode 115 is configured such that the high voltage pulse outputted from the high voltage generation device 114 should cause an insulation breakdown to occur.

The electromagnetic wave generation device 131 outputs a microwave of 2.45 GHz. In the electromagnetic wave generation device 131, a semiconductor oscillator generates the microwave. A semiconductor oscillator that oscillates a microwave of another frequency band may be employed.

The optical analysis device 140 performs component analysis of the target analyte 90 by analyzing an analysis light emitted from a plasma region P in which plasma of the target analyte 90 is generated by the plasma generation device 30. The optical analysis device 140 includes the optical probe 141, a spectroscope 142, an optical detector 143, and a signal processing device 144.

The optical probe 141 is a device for leading out a light emitted from the plasma region P in the internal space 120 of the casing 111. The optical probe 141 is a cylinder-like shaped case attached at a tip end part thereof with a lens capable of acquiring light from a relatively wide range of angle. The optical probe 141 is attached on the side surface of the casing 111 so that the light emitted from the entire plasma region P can be introduced to the lens. The optical probe 141 is connected to the spectroscope 142 via an optical fiber. The optical probe 141 may be omitted, and the optical fiber may directly acquire the light emitted from the plasma region P. Furthermore, as the lens of the optical probe 141, a condensing lens may be employed that is focused on the plasma region P.

The spectroscope 142 acquires the light incident to the optical probe 141. The spectroscope 142 spectrally disperses the incident light in various directions in accordance with wavelengths using a diffraction grating or a prism.

The spectroscope 142 is provided at an inlet thereof with a shutter for delimiting an analysis period of analyzing the light emitted from the plasma region P. The shutter is switched between an open state in which the light is allowed to be incident to the spectroscope 142 and a closed state in which the light is prohibited from being incident to the spectroscope 142. In a case in which the optical detector 143 is capable of controlling exposure timing, the analysis period may be delimited by controlling the optical detector 143.

The optical detector 143 is arranged so as to receive a light in a predetermined wavelength band from among the lights dispersed by the spectroscope 142. The optical detector 143, in response to an instruction signal outputted from the control device 135, performs photoelectric conversion on the light in the received wavelength band into electric signals for respective wavelengths. As the optical detector 143, for example, a charge coupled device is employed. The electric signal outputted from the optical detector 143 is inputted to the signal processing device 144.

The signal processing device 144 calculates a time integral value of emission intensity for each wavelength based on the electric signal outputted from the optical detector 143. The signal processing device 144 employs the light incident to the spectroscope 142 during the analysis period (while the shutter is in the open state) as the analysis light, and calculates time integral values (an emission spectrum) of emission intensity for respective wavelengths. The signal processing device 144 detects a wavelength component having strong emission intensity based on the time integral values of emission intensity for respective wavelengths, and identifies the material corresponding to the detected wavelength component as a component of the target analyte 90.

The transfer device 150 is a device that transfers the target analyte 90. The transfer device 150 moves a rod-like shaped supporting member 152 that supports the target analyte 90 by a motor power, for example. The supporting member 152 is inserted into the introduction window 101 and extends toward a side of the discharge gap. The transfer device 150 may be omitted, and the supporting member 152 may be manually moved.

<Operation of Analysis Device>

In the following, a description will be given of an analysis operation in which the analysis device 110 performs component analysis of the target analyte 90. During the analysis operation, a plasma generating and sustaining operation by the plasma generation device 30 and an optical analysis operation by the optical analysis device 140 are performed in conjunction with each other. When the plasma generating and sustaining operation has not yet started, the target analyte 90 locates outside of the plasma region P where the plasma will be sustained by the microwave. Although, according to the third embodiment, it is assumed that the target analyte 90 is a powder-like material, the target analyte 90 may be a non-powder material such as a piece of metal.

The plasma generating and sustaining operation will be firstly described hereinafter. The plasma generating and sustaining operation is an operation in which the plasma generation device 30 generates and sustains the plasma. The plasma generation device 30, under instruction of the control device 135, performs the plasma generating and sustaining operation of driving the discharge device 112 to generate discharge plasma and of driving the electromagnetic wave emission device 113 to irradiate the discharge plasma with the microwave, thereby maintaining the discharge plasma in the plasma state.

More particularly, the control device 135 outputs the discharge signal to the high voltage generation device 114. The high voltage generation device 114, upon receiving the discharge signal, outputs the high voltage pulse to the plug for discharge 100. In the plug for discharge 100, the discharge electrode 115 is supplied with the high voltage pulse. The spark discharge is generated at the discharge gap, and the discharge plasma is generated in a path of the spark discharge. The high voltage pulse is an impulse-like voltage signal having a peak voltage of, for example, 6 kV to 40 kV.

Immediately after the spark discharge, the control device 135 outputs the electromagnetic wave drive signal to the electromagnetic wave generation device 131. The electromagnetic wave generation device 131, upon receiving the electromagnetic wave drive signal, outputs the microwave as a CW (Continuous Wave) to the emission antenna 116. The microwave is emitted from the emission antenna 116 to the internal space 120 of the casing 111. The microwave is emitted from the emission antenna 116 during the period of time of the pulse width of the electromagnetic wave drive signal. An output timing of the electromagnetic wave drive signal is configured so that the microwave emission starts while the discharge plasma has not yet disappeared.

In the internal space 120 of the casing 111, a strong electric field region (a region having an electric field relatively strong in intensity in the internal space 120) is formed in the vicinity of the tip end of the emission antenna 116. The path of the spark discharge is included in the strong electric field region. The discharge plasma absorbs the microwave energy and is enlarged, thereby turning into ball-like microwave plasma. The microwave plasma is sustained during an emission period of the microwave. The emission period of the microwave constitutes a plasma sustain period.

During a former half of the plasma sustain period, the control device 135 outputs a transfer instruction to the transfer device 150. The transfer device 150, upon receiving the transfer instruction, moves the supporting member 152 to the plasma region P where the microwave plasma is present during the plasma sustain period. The target analyte 90 arranged at a tip end of the supporting member 152 penetrates into the plasma region P, and turns into the plasma state.

When the electromagnetic wave generation device 131 stops to output the microwave at a fall timing of the electromagnetic wave drive signal, the microwave plasma disappears. The emission period of the microwave is several tens of microseconds to several tens of seconds in length. A power output of the microwave is configured to be at a predetermined value (such as 80 watts) so that the microwave plasma should not turn into thermal plasma even in a case in which the electromagnetic wave generation device 131 outputs the microwave during a comparatively long period of time. Furthermore, the power output of the microwave is configured not to exceed 100 watts so that the powder-like target analyte 90 should not be dispersed.

Figure 7:
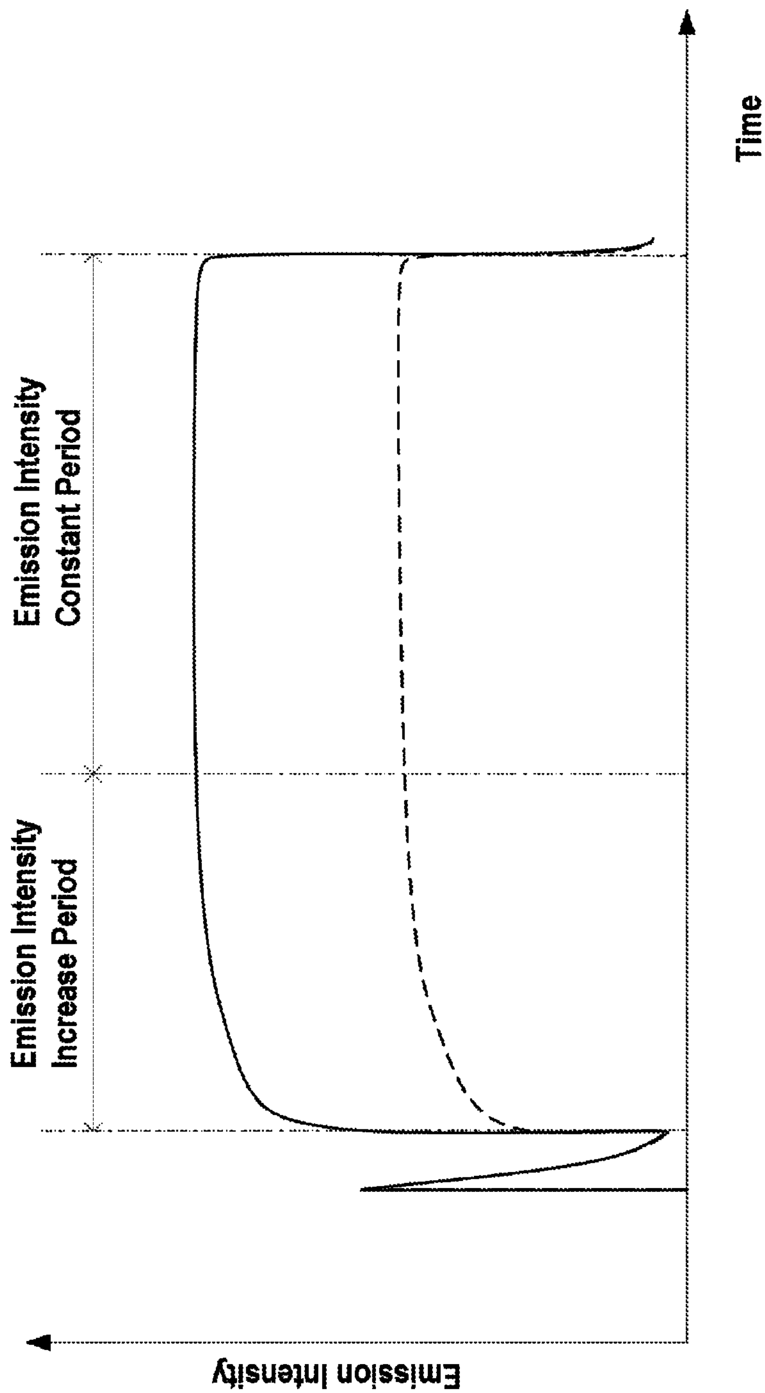
FIG. 7 is a graph illustrating a time series variation of emission intensity of a light emitted from plasma generated by a plasma generation device according to the third embodiment.

Referring to a time series variation of the emission intensity of a plasma light emitted from the plasma region P during a period from the generation of the discharge plasma to the disappearance of the microwave plasma, as shown in FIG. 7, there is initially observed an instantaneous peak in emission intensity of the discharge plasma, and the emission intensity decreases to a minimum value close to zero. After the emission intensity has reached the minimum value, there is observed an emission intensity increase period in which the emission intensity of the microwave plasma increases, and following the emission intensity increase period, there is observed an emission intensity constant period in which the emission intensity of the microwave becomes approximately constant, i.e., a period in which variation (increase) in emission intensity of the plasma light does not exceed a predetermined value.

In the plasma generation device 30 according to the third embodiment, as shown in FIG. 7 by a solid line, the power output of the microwave is configured so that a maximum value of the emission intensity in the plasma sustain period exceeds the peak value of the emission intensity at the time of the discharge plasma. As a result of this, it is possible to acquire the strong emission intensity from the plasma light while preventing the target analyte 90 from being dispersed, and thus, it is possible to analyze the target analyte 90 more accurately. However, in a case in which sufficient emission intensity is available, it may be configured such that the maximum value of the emission intensity in the plasma sustain period is made below the peak value of the emission intensity at the time of the discharge plasma, as shown in FIG. 7 by a broken line.

The optical analysis operation is an operation of analyzing the target analyte 90 by analyzing the analysis light emitted from the plasma region P in which the plasma of the target analyte 90 is generated by the plasma generation device 30. The optical analysis device 140 performs the optical analysis operation under instruction of the control device 135.

The optical analysis device 140 analyzes the analysis light emitted from the plasma region P during the plasma sustain period in which the plasma generation device 30 sustains the plasma by the microwave energy, thereby performs component analysis of the target analyte 90. The optical analysis device 140 sets an analysis period within the emission intensity constant period from the plasma sustain period, and analyzes the target analyte 90 based on the emission intensity of the plasma light during the analysis period. The control device 135, while controlling a shutter of the spectroscope 142, controls a period for the optical detector 143 to perform photoelectric conversion so that the entire emission intensity constant period should be set as the analysis period. Alternatively, apart of the emission intensity constant period may be set as the analysis period.

The optical analysis device 140 allows the plasma light to sequentially pass through the optical probe 141 and the optical fiber so as to be incident on the spectroscope 142 only during the emission intensity constant period (analysis period) shown in FIG. 7. The spectroscope 142 spectrally disperses the incident plasma light in different directions in accordance with wavelengths, and the plasma light in a predetermined wavelength band reaches the optical detector 143.

Figure 8:
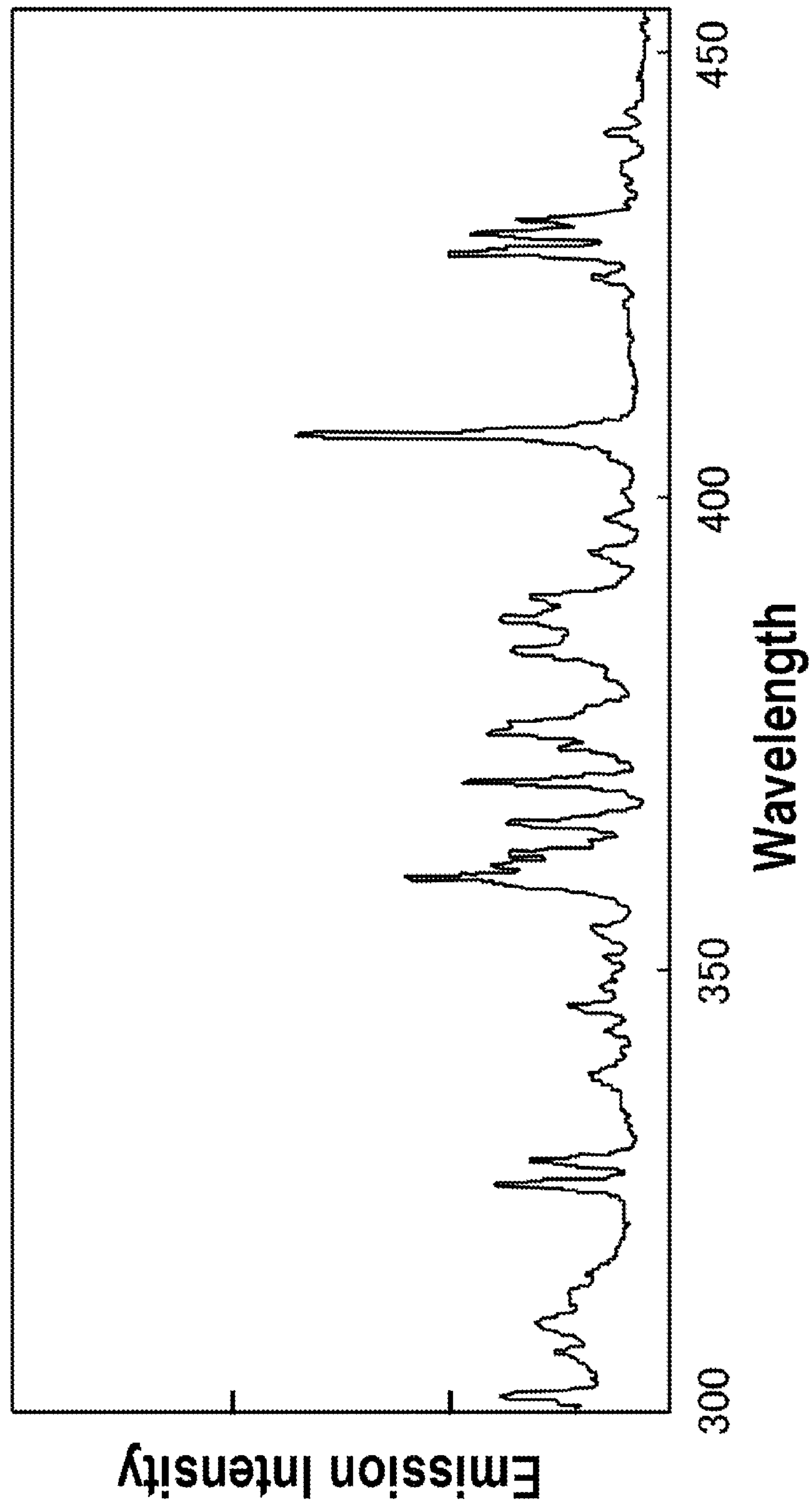
FIG. 8 is a spectrum illustrating time integral values of the emission intensity versus wavelengths with regard to the light emitted from the plasma generated by the plasma generation device according to the third embodiment.

The optical detector 143 performs photoelectric conversion on the plasma light in the received wavelength band into electric signals for respective wavelengths. The signal processing device 144 calculates time integral values of the emission intensity over the emission intensity constant period (analysis period) for respective wavelengths based on the output signals from the optical detector 143. The signal processing device 144 plots the spectrum, as shown in FIG. 8, illustrating the time integral values of emission intensity in accordance with wavelengths. The signal processing device 144 detects a wavelength at which the peak of the emission intensity appears from the time integral values of emission intensity in accordance with wavelengths, and identifies a material (atom or molecule) corresponding to the detected wavelength as the component of the target analyte 90.

The signal processing device 144 identifies the component of the target analyte 90 to be: molybdenum in a case in which the peak of the emission intensity appears at 379.4 mm wavelength, for example; calcium in a case in which the peak of the emission intensity appears at 422.7 mm wavelength, for example; cobalt in a case in which the peak of the emission intensity appears at 345.2 mm wavelength, for example; and chrome in a case in which the peak of the emission intensity appears at 357.6 mm wavelength, for example.

The signal processing device 144 may display the spectrum as shown in FIG. 8 on a monitor of the analysis device 110. A user of the analysis device 110 can identify the component of the target analyte by observing the spectrum.

<Effect of Third Embodiment>

According to the third embodiment, since the microwave energy is stably supplied to the plasma region P during the plasma sustain period, it is possible to prevent a shock wave from being generated by the microwave. The analysis period in which the optical analysis device 140 performs the analysis is configured to be within the plasma sustain period. Accordingly, it is possible to prevent the powder-like target analyte 90 in the plasma region P from being dispersed during the analysis period. It is possible to analyze the target analyte 90 in the plasma region P virtually without transferring the analyte.

Furthermore, according to the third embodiment, it is possible to analyze a powder-like material as it is. Conventionally, in a case in which a powder-like material is employed as the target analyte 90, the analysis has been performed on a pellet, into which the powder-like material is solidified by a binder. However, according to the third embodiment, since the powder-like material can be analyzed as it is, any noise caused by the binder will not show up in the emission intensity, and thus, it is possible to omit a filter to remove the noise.

Furthermore, according to the third embodiment, the microwave plasma is not so intense during the plasma sustain period. Accordingly, a metal constituting the emission antenna 116 is hardly excited, and thus, it is possible to suppress a noise caused by the excited metal.

<First Modified Example of Third Embodiment>

Figure 9:
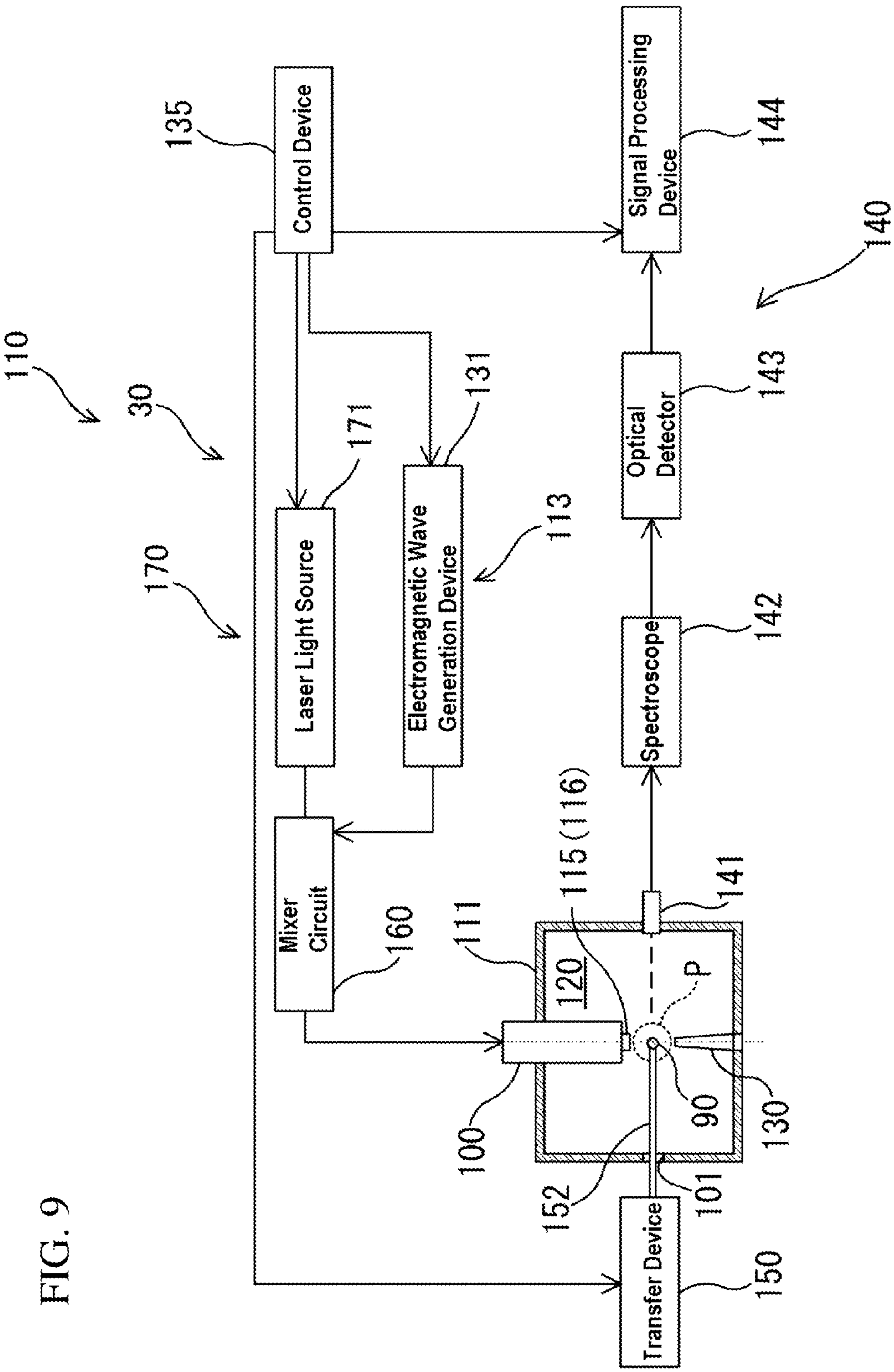
FIG. 9 is a schematic configuration diagram of an analysis device according to a first modified example of the third embodiment.

As shown in FIG. 9, the first modified example of the third embodiment is directed to an analysis device 110 that includes an auxiliary member 130, in addition to the casing 111, the plasma generation device 30, the optical analysis device 140, the transfer device 150, and the control device 135.

The plasma generation device 30 turns a material into plasma so as to generate initial plasma, and supplies the initial plasma with the microwave (electromagnetic wave) energy, thereby sustaining the plasma. The plasma generation device 30 includes a mixer circuit 160 in addition to the discharge device 112 and the electromagnetic wave emission device 113. The mixer circuit 160 is a circuit capable of mixing the microwave and the high voltage pulse. The mixer circuit 160 is supplied with the high voltage pulse from the high voltage generation device 114 and with the microwave from the electromagnetic wave generation device 131. The mixer circuit 160 outputs the high voltage pulse and the microwave to the plug for discharge 100. The discharge electrode 115 of the plug for discharge 100 is supplied with the microwave in addition to the high voltage pulse. The discharge electrode 115 functions as the emission antenna 116. In place of using the mixer circuit 160, the microwave may be supplied to the internal space 120 of the casing 111 via a waveguide from the electromagnetic wave generation device 131.

The auxiliary member 130 is a rod-like shaped electrically conductive member. The auxiliary member 130 protrudes from the lower surface of the casing Ill toward the discharge electrode 115 and extends to the vicinity of the discharge electrode 115. A distance between the auxiliary member 130 and the discharge electrode 115 is configured so that the high voltage pulse outputted from the high voltage generation device 114 causes an insulation breakdown to occur. The auxiliary member 130 forms the discharge gap together with the discharge electrode 115. The auxiliary member 130 is provided in the vicinity of the generation region in the internal space 120 on an opposite side of the discharge electrode 115 (the emission antenna 116) across the generation region.

According to the configuration described above, the plasma generation device 30, while causing the high voltage generation device 114 to output the high voltage pulse so as to generate the discharge plasma (initial plasma) at the discharge gap, causes the electromagnetic wave generation device 131 to output the microwave so as to emit the microwave from the discharge electrode 115 to the internal space 120, thereby sustaining the plasma.

Similarly to the third embodiment, the optical analysis device 140 analyzes the target analyte 90 by analyzing the light emitted from the plasma region P where the target analyte 90, which has been turned into plasma by the plasma generation device 30, is present.

According to the first modified example of the third embodiment, the electrically conductive auxiliary member 130 is arranged in the vicinity of the generation region where the initial plasma is generated, and the auxiliary member 130 concentrates the energy of the microwave supplied from the plasma generation device 30. Accordingly, since electric field intensity increases in a region where the plasma initially generated in the generation region is present, it is possible to effectively sustain the plasma.

<Second Modified Example of Third Embodiment>

Figure 10:
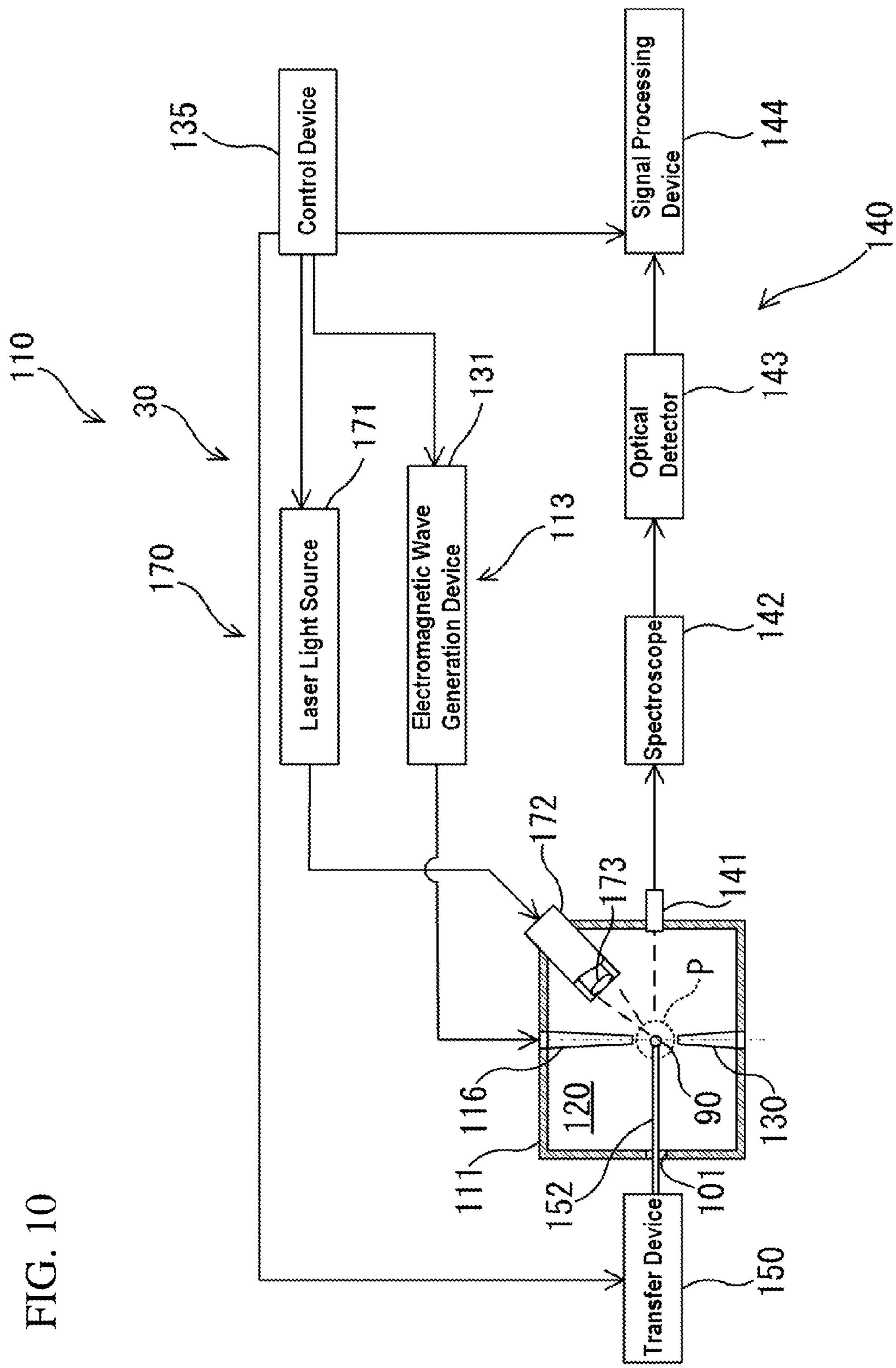
FIG. 10 is a schematic configuration diagram of an analysis device according to a second modified example of the third embodiment.

According to the second modified example of the third embodiment, as shown in FIG. 10, the analysis device 110 includes an auxiliary member 130, in addition to the casing 111, the plasma generation device 30, the optical analysis device 140, the transfer device 150, and the control device 135, similarly to the first modified example.

In place of the discharge device 112, the plasma generation device 30 includes a laser oscillation device 170. The laser oscillation device 170 generates the initial plasma by collecting a laser light. The laser oscillation device 170 includes a laser light source 171 and a probe for laser 172.

The laser light source 171, upon receiving a laser oscillation signal from the control device 135, oscillates the laser light for generating the initial plasma. The laser light source 171 is connected to the probe for laser 172 via an optical fiber. The probe for laser 172 is provided at a tip end thereof with a light collection optical system 173 that collects the laser light that has passed through the optical fiber. The probe for laser 172 is attached to the casing 111 so that the tip end thereof faces toward the internal space 120 of the casing 111. A focal point of the light collection optical system 173 locates at a central part of the casing 111. The laser light oscillated from the laser light source 171 passes through the light collection optical system 173 of the probe for laser 172 and is collected on the focal point of the light collection optical system 173.

In the laser oscillation device 170, a power output of the laser light source 171 is configured so that energy density of the laser light collected on the focal point of the light collection optical system 173 is not below a breakdown threshold value of a gas in the internal space 120. This means that the power output of the laser light source 171 is configured to be equal to or more than a value sufficient to turn a material existing at the focal point into plasma.

Furthermore, the casing 111 is attached on an upper surface thereof with the emission antenna 116, and on a lower surface thereof with the auxiliary member 130. The auxiliary member 130 is the same as that of the first modified example. The emission antenna 116 is formed in a rod-like shape and protrudes from the upper surface of the casing 111. A tip end of the emission antenna 116 is arranged in face-to-face relationship with a tip end of the auxiliary member 130 across the focal point of the light collection optical system 173.

According to the second modified example of the third embodiment, the electrically conductive auxiliary member 130 is arranged in the vicinity of a generation region where the plasma is initially generated, and the auxiliary member 130 concentrates the energy of the microwave supplied from the plasma generation device 30. Accordingly, in comparison with a case in which the auxiliary member 130 is not employed, electric field intensity increases in a region where the plasma initially generated in the generation region is present. Therefore, it is possible to effectively sustain the plasma.

<Other Embodiments>

The embodiments described above may also be configured as follows.

In the embodiments described above, by monitoring a reflection wave of the microwave during the emission period of the microwave, the microwave outputted from the electromagnetic wave generation device 31 may be varied in wavelength so that the reflection wave of the microwave should be reduced.

Furthermore, in the embodiments described above, in a case in which the receiving antenna 52 is covered by ceramic, a resonant frequency thereof changes depending on contamination condition of the ceramic. Therefore, an operation may be performed of detecting the resonant frequency of the receiving antenna 52 at a start-up time or the like of the internal combustion engine 10. Based on the detected resonant frequency, an oscillation frequency of the microwave is adjusted so that a resonance occurs at the receiving antenna 52.

Furthermore, in the embodiments described above, the emission antenna 16 may be covered by a dielectric.

Furthermore, in the third embodiment described above, the target analyte 90 may be transferred to the plasma region P while the discharge plasma has not yet been generated.

INDUSTRIAL APPLICABILITY

From the foregoing description, it is to be understood that the present invention is useful in relation to a plasma generation device that utilizes energy of an electromagnetic wave, an internal combustion engine that includes the plasma generation device, and an analysis device that includes the plasma generation device.

EXPLANATION OF REFERENCE NUMERALS

10 Internal Combustion Engine
11 Internal Combustion Engine Main Body
12 Ignition Device
13 Electromagnetic Wave Emission Device
14 Ignition Coil (High Voltage Generation Device)
15 Discharge Electrode
16 Emission Antenna
20 Combustion Chamber
30 Plasma Generation Device
31 Electromagnetic Wave Generation Device

What is claimed is:

1. A plasma generation device comprising:

an electromagnetic wave generation device that generates an electromagnetic wave;

an emission antenna for emitting the electromagnetic wave outputted from the electromagnetic wave generation device to a target space;

a voltage generation device that generates a voltage; and a discharge electrode that is provided in the target space and is applied with the voltage outputted from the voltage generation device, wherein the emission antenna forms a discharge gap together with the discharge electrode, the plasma generation device enlarges discharge plasma using the electromagnetic wave emitted from the emission antenna caused by the electromagnetic wave outputted from the electromagnetic wave generation device, where the discharge plasma is generated at the discharge gap by an output of a voltage from the voltage generation device, and the emission antenna is electrically grounded.

2. The plasma generation device according to claim 1, wherein the emission antenna is formed in a shape that surrounds the discharge electrode.

3. A plasma generation device comprising:

an electromagnetic wave generation device that generates an electromagnetic wave;

an emission antenna for emitting the electromagnetic wave outputted from the electromagnetic wave generation device to a target space;

a voltage generation device that generates a voltage; and a discharge electrode that is provided in the target space and is applied with the voltage outputted from the voltage generation device, wherein the emission antenna forms a discharge gap together with the discharge electrode, and the plasma generation device enlarges discharge plasma using the electromagnetic wave emitted from the emission antenna caused by the electromagnetic wave outputted from the electromagnetic wave generation device, where the discharge plasma is generated at the discharge gap by an output of a voltage from the voltage generation device, the plasma generation device includes in the target space a secondary electrode provided in a state of being electrically grounded or floating at a location where a discharge does not occur between the discharge electrode and the secondary electrode even if a voltage is applied to the discharge electrode from the voltage generation device, and a second discharge gap is formed between the emission antenna and the secondary electrode, assuming that the discharge gap between the emission antenna and the discharge electrode as a first discharge gap.

4. An internal combustion engine comprising:

a plasma generation device according to claim 1; and an internal combustion engine main body formed with a combustion chamber, wherein the emission antenna and the discharge electrode are provided in the internal combustion engine main body so that the discharge gap locates in the combustion chamber.

5. An analysis device comprising:

a plasma generation device according to claim 1, which is adapted to turn a target analyte into a plasma state; and an optical analysis device that analyzes the target analyte by analyzing analysis light emitted from a region where the plasma of the target analyte is generated by the plasma generation device.

6. The analysis device according to claim 5, wherein the analysis device includes a casing, which is provided with the emission antenna and the discharge electrode, and partitions the target space, and the emission antenna is formed in a rod-like shape and protrudes toward the discharge electrode from a surface facing toward a surface having the discharge electrode provided thereon from among surfaces of the casing.

7. The analysis device according to claim 5, wherein the plasma generation device sustains the plasma enlarged by the electromagnetic wave by continuously emitting the electromagnetic wave from the emission antenna, and the optical analysis device analyzes the target analyte using a time integral value of emission intensity of the analysis light over a plasma sustain period during which the plasma generation device sustains the plasma.

8. The analysis device according to claim 7, wherein the plasma generation device causes the emission antenna to emit the electromagnetic wave as a continuous wave during the plasma sustain period.

9. The analysis device according to claim 8, wherein during the plasma sustain period, the target analyte is transferred to a region where the plasma sustained by the plasma generation device is present, and turned into the plasma state.

10. The plasma generation device according to claim 2, wherein the emission antenna is formed in a shape of a letter C or a ring in a manner to surround the discharge electrode.

11. A plasma generation device comprising:

an electromagnetic wave generation device that generates an electromagnetic wave;

an emission antenna for emitting the electromagnetic wave outputted from the electromagnetic wave generation device to a target space;

a voltage generation device that generates a voltage; and a discharge electrode that is provided in the target space and is applied with the voltage outputted from the voltage generation device, wherein the emission antenna forms a discharge gap together with the discharge electrode, the plasma generation device enlarges discharge plasma using the electromagnetic wave emitted from the emission antenna caused by the electromagnetic wave outputted from the electromagnetic wave generation device, where the discharge plasma is generated at the discharge gap by an output of a voltage from the voltage generation device, and the emission antenna is formed in a shape of a letter C or a ring in a manner to surround the discharge electrode.

* * * * *